United States Patent
Ingvarsson

(10) Patent No.: US 11,617,965 B2
(45) Date of Patent: Apr. 4, 2023

(54) PROCESS OF SPRAY DRYING OF GLP-1 PEPTIDE

(71) Applicant: Novo Nordisk A/S, Bagsvaerd (DK)

(72) Inventor: Pall Thor Ingvarsson, Kopavogur (IS)

(73) Assignee: Novo Nordisk A/S, Bagsvaerd (DK)

( * ) Notice: Subject to any disclaimer, the term of this patent is extended or adjusted under 35 U.S.C. 154(b) by 19 days.

(21) Appl. No.: 17/415,623

(22) PCT Filed: Dec. 20, 2019

(86) PCT No.: PCT/EP2019/086645
§ 371 (c)(1),
(2) Date: Jun. 17, 2021

(87) PCT Pub. No.: WO2020/127950
PCT Pub. Date: Jun. 25, 2020

(65) Prior Publication Data
US 2022/0088500 A1   Mar. 24, 2022

(30) Foreign Application Priority Data

Dec. 21, 2018 (EP) .................................. 18215348

(51) Int. Cl.
B01D 1/18 (2006.01)
A23K 20/184 (2016.01)
A61K 38/26 (2006.01)
B01D 1/20 (2006.01)

(52) U.S. Cl.
CPC .............. *B01D 1/18* (2013.01); *A23K 20/184* (2016.05); *A61K 38/26* (2013.01); *B01D 1/20* (2013.01)

(58) Field of Classification Search
CPC ........... B01D 1/18; B01D 1/20; A23K 20/184
See application file for complete search history.

(56) References Cited

U.S. PATENT DOCUMENTS

| 9,387,176 B2 * | 7/2016 | Havelund | .................. A61P 3/10 |
| 2010/0179090 A1 * | 7/2010 | Havelund | .............. A61K 38/26 |
| | | | 514/1.1 |
| 2010/0183876 A1 * | 7/2010 | Hell | .......................... A61K 9/14 |
| | | | 530/308 |
| 2013/0172271 A1 * | 7/2013 | Fragale | ................ A61K 31/675 |
| | | | 514/21.1 |

(Continued)

FOREIGN PATENT DOCUMENTS

| CN | 106924750 A | 7/2017 |
| CN | 108745218 A | 11/2018 |

(Continued)

OTHER PUBLICATIONS

Ingvarsson et al. "Engineering of an inhalable DDA/TDB liposomal adjuvant: a quality-by-design approach towards optimization of the spray drying process." Pharmaceutical research, 2013, vol. 30, No. 11, pp. 2772-2784.

(Continued)

*Primary Examiner* — Jonathan Miller
(74) *Attorney, Agent, or Firm* — Leon Y. Lum

(57) ABSTRACT

The present invention relates to a process for spray drying of a feed solution comprising the GLP-1 peptide semaglutide wherein the ratio of atomising gas flow (kg/h) to feed solution flow (kg/h) is 1.0-1.7.

26 Claims, 3 Drawing Sheets

(56) References Cited

U.S. PATENT DOCUMENTS

| 2015/0150811 | A1* | 6/2015 | Jensen | A61P 3/04 |
| | | | | 424/464 |
| 2017/0014789 | A1 | 1/2017 | Santos et al. | |
| 2017/0252409 | A1 | 9/2017 | Leung | |
| 2019/0224584 | A1* | 7/2019 | Dobry | C11D 11/02 |

FOREIGN PATENT DOCUMENTS

| WO | 9847493 | A1 | 10/1998 |
| WO | 0066256 | A1 | 11/2000 |
| WO | 2001/093837 | A2 | 12/2001 |
| WO | 02/098348 | A2 | 12/2002 |
| WO | 2008/132224 | A2 | 11/2008 |
| WO | 08133908 | A2 | 11/2008 |
| WO | 10072621 | A2 | 7/2010 |
| WO | 2013139694 | A1 | 9/2013 |
| WO | 2013189988 | A1 | 12/2013 |
| WO | 2014191545 | A1 | 12/2014 |
| WO | 2017186896 | A1 | 11/2017 |

OTHER PUBLICATIONS

Kemp et al."Experimental study of spray drying and atomization with a two-fluid nozzle to produce inhalable particles." Drying Technology, 2013, vol. 31, No. 8, pp. 930-941.
Lebrun et al. "Design space approach in the optimization of the spray-drying process." European Journal of Pharmaceutics and Biopharmaceutics, 2012, vol. 80, No. 1, pp. 226-234.
Liang et al. "Factors influencing flow pattrens, temperature fields and consequent drying rates in spray drying." Drying Technology, 1991, vol. 9, No. 1, pp. 1-25.
Maltesen et al.,"Quality by design—Spray drying of insulin intended for inhalation." European Journal of Pharmaceutics and Biopharmaceutics, 2008, vol. 70, No. 3, pp. 828-838.
Mosen et al., "Particle formation and capture during spray drying of inhalable particles." Pharmaceutical development and technology, 2005, vol. 9, No. 4, pp. 409-417.
Qian et al. "Pulmonary delivery of a GLP-1 receptor agonist, BMS-686117." International journal of pharmaceutics, Jan. 2009, vol. 366, No. 1-2, pp. 218-220.

* cited by examiner

PROCESS OF SPRAY DRYING OF GLP-1 PEPTIDE

CROSS-REFERENCE TO RELATED APPLICATIONS

This application is a 35 U.S.C. § 371 National Stage application of International Application PCT/EP2019/086645 (WO/2020/127950), filed Dec. 20, 2019, which claims priority to European Patent Application 18215348.6, filed Dec. 21, 2018; the contents of which are incorporated herein by reference.

The present invention relates to the field of spray drying of a feed solution comprising a GLP-1 peptide, e.g. semaglutide. More specifically, the invention pertains to processes for spray drying of a feed solution comprising semaglutide wherein an improved yield is obtained, semaglutide obtainable by said process and its use in medicine.

BACKGROUND

Process yield is of high importance in securing reduced production costs of drug products. During spray drying of drug substances, product is inevitably lost e.g. to the walls of the spray dryer. It is highly desired to obtain processes for spray drying of drug substances, wherein as little product as possible is lost during the drying process and wherein the highest possible yield is obtained.

SUMMARY

In some embodiments, the invention relates to a process for spray drying of a feed solution comprising semaglutide, wherein the process comprises introducing the feed solution comprising semaglutide into a spray dryer at a feed flow rate (kg/h) and introducing an atomising gas into the spray dryer at an atomising gas flow rate (kg/h), wherein the ratio of atomising gas flow rate (kg/h) to feed flow rate (kg/h) is 1.0-1.7.

DESCRIPTION

Figure 1:
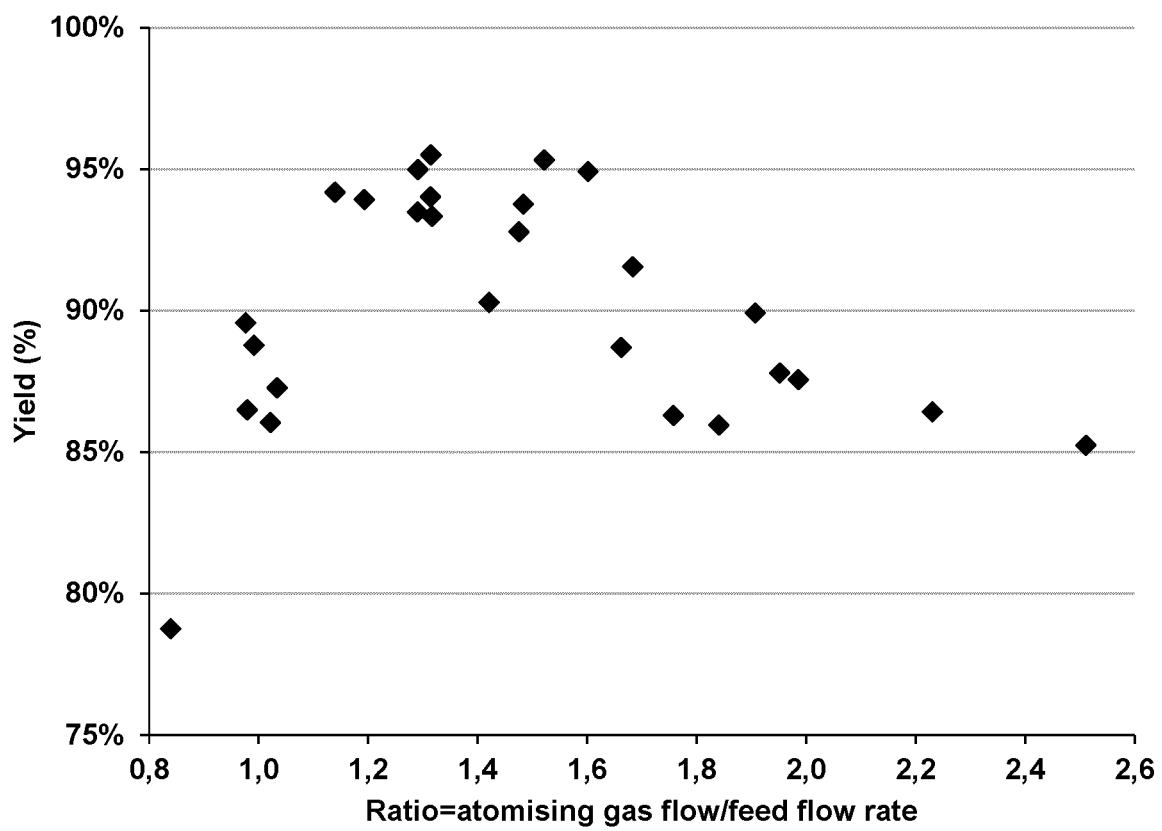
FIG. 1 is a plot of the data from laboratory scale experiments of semaglutide in aqueous ethanol (Example 1, Table 3). It is seen that when the ratio of atomising gas flow rate (kg/h)/feed flow rate (kg/h) is between 1.1-1.7, then a higher yield is obtained compared to experiments performed outside the specified ratio.

Spray drying is often used as a step in the manufacture of drug substances and drug products and the yield of this process is important for the overall product costs of the final drug product. Several parameters influence the yield obtained, e.g. it is generally recognized that a higher outlet temperature results in a higher yield. This is because at a higher temperature then dryer particles are obtained which are less prone to stick to the inner wall of the spray dryer upon collision.

The present inventors have observed that upon spray drying of a feed solution comprising a GLP-1 peptide, e.g. semaglutide, minimal difference in yield is seen by increasing the outlet temperature. Instead, it is surprisingly seen that the ratio between the atomising gas flow rate (kg/h) and the feed flow rate (kg/h) is of higher importance for obtaining an increased yield. In some embodiments, a higher yield is obtained when the ratio between the atomising gas flow (kg/h) and the feed flow (kg/h) is in the range 1.0-1.7. The ratio of atomising gas flow rate in kg/h to feed flow rate in kg/h is substantially independent of the apparatus used (e.g. laboratory scale vs. production scale) and the outlet temperature. So even though atomising gas flow rate and feed flow rate differ substantially between scales, the ratio of atomising gas flow rate to feed flow rate can be operated within the same range.

Process for Spray Drying

The present invention concerns a process for spray drying of a feed solution comprising a GLP-1 peptide. In one embodiment, the present invention concerns a process for spray drying of a feed solution comprising the GLP-1 peptide semaglutide, said process comprising introducing a feed solution comprising semaglutide in a solvent into the spray dryer at a feed flow rate and introducing an atomising gas at an atomising gas flow rate, wherein the ratio of atomising gas flow rate (kg/h) to feed flow rate (kg/h) is 1.0-1.7. In some embodiments, the ratio of atomising gas flow rate (kg/h) to feed flow rate (kg/h) is 1.1-1.7 or 1.2-1.7.

In some embodiments, the feed solution comprises a solution of a GLP-1 peptide in a solvent. In some embodiments, the feed solution comprises a solution of GLP-1 peptide semaglutide in a solvent. In some embodiments, the solvent is an aqueous organic solvent, such as ethanol or acetonitrile, i.e. a water miscible organic solvent. In some embodiments, the solvent is an aqueous alcoholic solvent such as aqueous ethanol, i.e. comprising water and ethanol. In some embodiments, the feed solution consists substantially of semaglutide in aqueous ethanol. In some embodiments, the aqueous ethanol is in a concentration of 40-70% (w/w), such as 45-60% (w/w) or 48-53% (w/w). The concentration of aqueous ethanol is defined from the content of ethanol, i.e. 70% (w/w) aqueous ethanol consists substantially of 70% ethanol and 30% water by weight. In some embodiments, the solvent is aqueous acetonitrile, i.e. comprising water and acetonitrile. In some embodiments, the feed solution consists substantially of semaglutide in aqueous acetonitrile. In some embodiments, the aqueous acetonitrile is in a concentration of 40-70% (w/w), such as 45-60% (w/w) or 48-55% (w/w). The concentration of aqueous acetonitrile is defined from the content of acetonitrile, i.e. 70% (w/w) aqueous acetonitrile consists substantially of 70% acetonitrile and 30% water by weight.

In some embodiments, the concentration of semaglutide in the feed solution is 0.5-10% (w/w), such as 1-5% (w/w) or 1-3% (w/w). In some embodiments, the feed solution comprises 2.0-2.5% (w/w) semaglutide in 48-53% (w/w) aqueous ethanol. In some embodiments, the feed solution consists substantially of 2.0-2.5% (w/w) semaglutide in 48-53% (w/w) aqueous ethanol. In some embodiments, the feed solution comprises 2.0-2.5% (w/w) semaglutide in 50-55% (w/w) aqueous acetonitrile. In some embodiments, the feed solution consists essentially of 2.0-2.5% (w/w)

semaglutide in 50-55% (w/w) aqueous acetonitrile. As used herein, 'the feed solution consists substantially of semaglutide', refers to that other agents from the manufacturing process may be present, e.g. salts or peptide impurities; for example, the main component is semaglutide and no excipients have been added. In some embodiments, the feed solution introduced into the spray dryer comes from a final chromatographic manufacturing step and will as a main component comprise semaglutide (80-100%), but also e.g. salts and impurities carried over from manufacture.

In some embodiments, the feed solution is introduced into a spray drying chamber at a feed flow rate of 20-60 kg/h, such as 36-56 kg/h or 41-51 kg/h.

The atomising gas is used to atomise the feed solution into a spray drying chamber. In some embodiments, the atomising gas is air or nitrogen. In some embodiments, the atomising gas is introduced at an atomising gas flow rate of 20-80 kg/h. In some embodiments, the atomising gas flow rate is 30-77 kg/h. In some embodiments, the atomising gas flow rate is 52-62 kg/h.

A nozzle is used to atomise the feed solution, i.e. transform the feed solution into a spray of small particles. The feed solution and the atomising gas are introduced into the spray drying chamber via a nozzle. In some embodiments, the nozzle used has at least two fluid entry channels, such as a two-fluid nozzle or a three-fluid nozzle. In some embodiments, the nozzle is a two-fluid nozzle e.g. having an inside diameter of 1.0 mm with cap of 5 mm or 6.5 mm.

A drying gas is employed to dry the atomised feed solution in the spray drying chamber. In some embodiments, the drying gas is air or nitrogen. In some embodiments, the drying gas is introduced at an inlet temperature ($T_{in}$) of 85-200° C. In some embodiments, the inlet temperature is 100-180° C., e.g. 120-160° C. The inlet temperature is adjusted to maintain the desired set points of outlet temperature, feed flow rate, atomising gas flow rate and drying gas flow rate, and may therefore vary depending on said parameters as describes in the examples. In some embodiments, the outlet temperature ($T_{out}$) of the drying gas is 50-100° C., such as 55-90° C. In some embodiments, the drying gas flow rate is 1000-1800 kg/h. In some embodiments, the drying gas flow rate is 1200-1750 kg/h, such as 1300-1400 kg/h or 1345-1355 kg/h.

In some embodiments, the process comprises introducing the feed solution comprising semaglutide in a solvent into the spray dryer at a feed flow rate (kg/h) and introducing the atomising gas into the spray dryer at an atomising gas flow rate (kg/h), wherein the ratio of atomising gas flow rate (kg/h) to feed flow rate (kg/h) is 1.0-1.7.

In some embodiments, the process comprises introducing the feed solution comprising semaglutide in a solvent into the spray dryer at a feed flow rate of 20-60 kg/h and introducing the atomising gas into the spray dryer at an atomising gas flow rate of 20-80 kg/h, wherein the ratio of atomising gas flow rate (kg/h) to feed flow rate (kg/h) is 1.0-1.7.

In some embodiments, the process comprises introducing the feed solution comprising semaglutide in a solvent into the spray dryer at a feed flow rate of 20-60 kg/h and introducing the atomising gas into the spray dryer at an atomising gas flow rate of 20-80 kg/h, wherein the ratio of atomising gas flow rate (kg/h) to feed flow rate (kg/h) is 1.0-1.7 and the outlet temperature is 55-90° C.

In some embodiments, the process comprises introducing the feed solution comprising 0.5-10% (w/w) semaglutide in 40-70% (w/w) aqueous ethanol into the spray dryer at a feed flow rate of 20-60 kg/h and introducing the atomising gas into the spray dryer at an atomising gas flow rate of 20-80 kg/h, wherein the ratio of atomising gas flow rate (kg/h) to feed flow rate (kg/h) is 1.0-1.7.

In some embodiments, the process comprises introducing the feed solution comprising 0.5-10% (w/w) semaglutide in 40-70% (w/w) aqueous ethanol into the spray dryer at a feed flow rate of 20-60 kg/h and introducing the atomising gas into the spray dryer at an atomising gas flow rate of 20-80 kg/h, wherein the ratio of atomising gas flow rate (kg/h) to feed flow rate (kg/h) is 1.0-1.7 and an outlet temperature of 55-90° C.

In some embodiments, the process comprises introducing the feed solution comprising 2.0-2.5% (w/w) semaglutide in 48-53% (w/w) aqueous ethanol into the spray drying chamber via a two-fluid nozzle with a feed flow rate of 41-51 kg/h and an atomising gas at an atomising flow rate of 52-62 kg/h, wherein the drying gas flow rate is 1345-1355 kg/h with an inlet temperature of 120-160° C. and an outlet temperature of 55-90° C., and the drying gas and atomising gas are both nitrogen.

In some embodiment, the process comprises introducing the feed solution comprising 2.0-2.2% (w/w) semaglutide in 50-55% (w/w) aqueous ethanol into the spray dryer chamber via a two-fluid nozzle with a feed flow rate of 45-47 kg/h and an atomising gas flow of 55-59 kg/h resulting in a ratio of 1.2, wherein the drying gas flow rate is 1348-1355 kg/h, outlet temperature of 73° C. and the drying gas and atomising gas are both nitrogen. The inlet temperature is adjusted accordingly, e.g. to an inlet temperature in the interval of 130-150° C. In a specific embodiment, the process comprises introducing the feed solution comprising 2.1% (w/w) semaglutide in 53% (w/w) aqueous ethanol into the spray dryer chamber via a two-fluid nozzle with a feed flow rate of 46 kg/h and an atomising gas flow of 57 kg/h resulting in a ratio of 1.2, wherein the drying gas flow rate is 1350 kg/h, outlet temperature of 73° C. and the drying gas and atomising gas are both nitrogen. The inlet temperature is adjusted accordingly, e.g. to an inlet temperature of 130-150° C. or 137-139° C.

In some embodiments, the process comprises introducing the feed solution comprising 0.5-10% (w/w) semaglutide in 40-70% (w/w) aqueous acetonitrile into the spray dryer at a feed flow rate of 20-60 kg/h and introducing the atomising gas into the spray dryer at an atomising gas flow rate of 20-80 kg/h, wherein the ratio of atomising gas flow rate (kg/h) to feed flow rate (kg/h) is 1.0-1.7.

In some embodiments, the process comprises introducing the feed solution comprising 0.5-10% (w/w) semaglutide in 40-70% (w/w) aqueous acetonitrile into the spray dryer at a feed flow rate of 20-60 kg/h and introducing the atomising gas into the spray dryer at an atomising gas flow rate of 20-80 kg/h, wherein the ratio of atomising gas flow rate (kg/h) to feed flow rate (kg/h) is 1.0-1.7 and an outlet temperature of 55-90° C.

In some embodiments, the process comprises introducing the feed solution comprising 2.0-2.5% (w/w) semaglutide in 48-53% (w/w) aqueous acetonitrile into the spray drying chamber via a two-fluid nozzle with a feed flow rate of 41-51 kg/h and an atomising gas at an atomising flow rate of 52-62 kg/h, wherein the drying gas flow rate is 1345-1355 kg/h, an outlet temperature of 55-90° C., and the drying gas and atomising gas are both nitrogen. The inlet temperature is adjusted accordingly, e.g. to an inlet temperature of 100-160° C.

Semaglutide

The GLP-1 peptide semaglutide may be prepared as described in WO2006/097537, Example 4. Semaglutide is also known as $N^{6,26}$-{18-[N-(17-carboxyheptadecanoyl)-L-γ-glutamyl]-10-oxo-3,6,12,15-tetraoxa-9,18-diazaoctadecanoyl}-[8-(2-amino-2-propanoic acid), 34-L-arginine]human glucagon-like peptide 1(7-37), see WHO Drug Information Vol. 24, No. 1, 2010 and has the following structure:

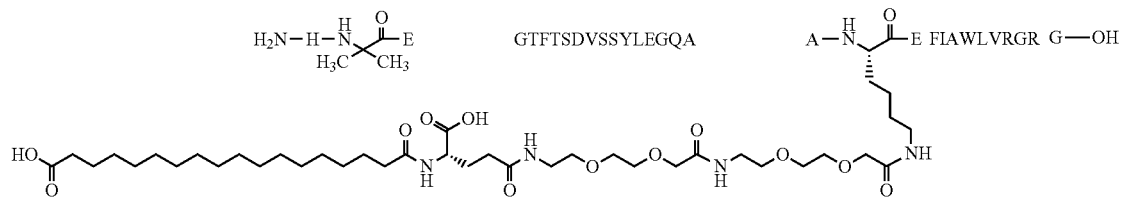

In some embodiments, semaglutide may be present in its fully or partly ionised form; for example one or more carboxylic acid groups (—COOH) may be deprotonated into the carboxylate group (—COO$^-$) and/or one or more amino groups (—NH$_2$) may be protonated into the —NH$_3{}^+$ groups. In some embodiments, semaglutide is in the form of a salt.

Uses

The product obtainable by the process of the invention is intended for use in a pharmaceutical composition together with one or more pharmaceutically acceptable excipients. In some embodiments, the product obtainable by the process of the invention is for subcutaneous administration. In some embodiments, the product obtainable by the process is for oral administration, e.g. in the form of a tablet.

In some embodiments, the product obtainable by the process of the invention is for use in medicine.

In some embodiments, the product obtainable by the process of the invention may be used in the treatment or prevention of type 2 diabetes and/or obesity.

Unless otherwise indicated in the specification, terms presented in singular form also include the plural form.

In some embodiments, as used herein, specific values given in relation to numbers or intervals may be understood as the specific value or as about the specific value (e.g. plus or minus 10 percent of the specific value).

EMBODIMENTS

The following are non-limiting embodiments of the invention:
1. A process for spray drying of a feed solution comprising semaglutide, said process comprising introducing the feed solution comprising semaglutide in a solvent into a spray dryer at a feed flow rate and introducing an atomising gas at an atomising gas flow rate, wherein the ratio of atomising gas flow rate (kg/h) to feed flow rate (kg/h) is in the range 1.0-1.7.
2. The process according to embodiment 1, wherein the ratio of atomising gas flow rate (kg/h) to feed flow rate (kg/h) is in the range 1.1-1.7.
3. The process according to any one of the preceding embodiments, wherein the ratio of atomising gas flow rate (kg/h) to feed flow rate (kg/h) is in the range 1.2-1.7.
4. The process according to any one of the preceding embodiments, wherein the ratio of atomising gas flow rate (kg/h) to feed flow rate (kg/h) is in the range 1.2-1.6.
5. The process according to any one of the preceding embodiments, wherein the ratio of atomising gas flow rate (kg/h) to feed flow rate (kg/h) is in the range 1.2-1.5.
6. The process according to any one of the preceding embodiments, wherein the feed flow rate is 20-60 kg/h.
7. The process according to any of the preceding embodiments, wherein the feed flow rate is 30-58 kg/h.
8. The process according to any of the preceding embodiments, wherein the feed flow rate is 35-56 kg/h.
9. The process according to any of the preceding embodiments, wherein the feed flow rate is 41-51 kg/h.
10. The process according to any of the preceding embodiments, wherein the atomising gas flow rate is 20-80 kg/h.
11. The process according to any one of the preceding embodiments, wherein the atomising gas flow rate is 30-77 kg/h.
12. The process according to any one of the preceding embodiments, wherein the atomising gas flow rate is 38-65 kg/h.
13. The process according to any one of the preceding embodiments, wherein the atomising gas flow rate is 52-62 kg/h.
14. The process according to any one of the preceding embodiments, wherein the feed solution consists substantially of semaglutide in a solvent.
15. The process according to any one of the preceding embodiments, wherein the feed solution solvent comprises a water miscible organic solvent.
16. The process according to any one of the preceding embodiments, wherein the feed solution solvent comprises an organic alcoholic solvent.
17. The process according to any one of the preceding embodiments, wherein the feed solution solvent comprises ethanol.
18. The process according to any one of the preceding embodiments, wherein the feed solution solvent is aqueous ethanol.
19. The process according to any one of the preceding embodiments, wherein the feed solution solvent is 40-70% (w/w) aqueous ethanol.
20. The process according to any one of the preceding embodiments, wherein the feed solution solvent is 45-60% (w/w) aqueous ethanol.
21. The process according to any one of the preceding embodiments, wherein the feed solution solvent is 48-55% (w/w) aqueous ethanol.
22. The process according to any one of the preceding embodiments, wherein the feed solution solvent is 48-53% (w/w) aqueous ethanol.
23. The process according to any one of embodiments 1-15, wherein the feed solution solvent comprises acetonitrile.

24. The process according to any one of embodiments 1-15 or 23, wherein the feed solution solvent is aqueous acetonitrile.
25. The process according to any one of embodiments 1-15 or 23-24, wherein the feed solution solvent is 40-70% (w/w) aqueous acetonitrile.
26. The process according to any one of embodiments 1-15 or 23-25, wherein the feed solution solvent is 45-60% (w/w) aqueous acetonitrile.
27. The process according to any one of embodiments 1-15 or 23-26, wherein the feed solution solvent is 48-55% (w/w) aqueous acetonitrile.
28. The process according to any one of the preceding embodiments, wherein the feed solution comprises 0.5-10% (w/w) semaglutide.
29. The process according to any one of the preceding embodiments, wherein the feed solution comprises 1-5% (w/w) semaglutide.
30. The process according to any one of the preceding embodiments, wherein the feed solution comprises 1-3% (w/w) semaglutide.
31. The process according to any one of the preceding embodiments, wherein the feed solution comprises 2.0-2.5% (w/w) semaglutide.
32. The process according to any one of the preceding embodiments, wherein the feed solution comprises 2.0-2.5% (w/w) semaglutide in 48-53% (w/w) aqueous ethanol.
33. The process according to any one of the preceding embodiments, wherein the feed solution consists substantially of 2.0-2.5% (w/w) semaglutide in 48-53% (w/w) aqueous ethanol.
34. The process according to any one of embodiments 1-15 or 23-31, wherein the feed solution comprises 2.0-2.5% (w/w) semaglutide in 48-55% (w/w) aqueous acetonitrile.
35. The process according to any one of embodiments 1-15 or 23-31, wherein the feed solution consists substantially of 2.0-2.5% (w/w) semaglutide in 48-55% (w/w) aqueous acetonitrile.
36. The process according to any one of the preceding embodiments, wherein the atomising gas is nitrogen or air.
37. The process according to any one of the preceding embodiments, wherein the atomising gas is nitrogen.
38. The process according to any one of the preceding embodiments, wherein the drying gas is nitrogen or air.
39. The process according to any one of the preceding embodiments, wherein the drying gas is nitrogen.
40. The process according to any one of the preceding embodiments, wherein the atomising gas and the drying gas are both nitrogen.
41. The process according to any one of the preceding embodiments, wherein the outlet temperature is 50-100° C.
42. The process according to any one of the preceding embodiments, wherein the outlet temperature is 55-90° C.
43. The process according to any one of the preceding embodiments, wherein the outlet temperature is 68-80° C.
44. The process according to any one of the preceding embodiments, wherein the inlet temperature is adjusted to maintain desired set points of outlet temperature, atomising gas flow rate, feed flow rate and drying gas flow rate.
45. The process according to any one of the preceding embodiments, wherein the inlet temperature is 85-200° C.
46. The process according to any one of the preceding embodiments, wherein the inlet temperature is 100-180° C.
47. The process according to any one of the preceding embodiments, wherein the inlet temperature is 120-160° C.
48. The process according to any one of the preceding embodiments, wherein the drying gas flow rate is 1000-1800 kg/h.
49. The process according to any one of the preceding embodiments, wherein the drying gas flow rate is 1200-1750 kg/h.
50. The process according to any one of the preceding embodiments, wherein the drying gas flow rate is 1300-1400 kg/h.
51. The process according to any one of the preceding embodiments, wherein the drying gas flow rate is 1345-1355 kg/h.
52. The process according to any one of the preceding embodiments, wherein the nozzle used for atomising has at least two-fluid entry channels, such as a two-fluid nozzle or a three-fluid nozzle.
53. The process according to anyone of the preceding embodiments, wherein the nozzle used is a two-fluid nozzle.
54. The process according to any one of the preceding embodiments, wherein the nozzle used has an inside diameter of 1.0 mm with cap of 5 mm or 6.5 mm.
55. The process according to any one of the preceding embodiments, wherein the nozzle used has an inside diameter of 1.0 mm with cap of 6.5 mm.
56. The product obtainable by the process according to any one of the preceding embodiments.
57. A pharmaceutical composition comprising a therapeutically effective amount of the product according to embodiment 56.
58. The pharmaceutical composition according to embodiment 57 in the form of a tablet.
59. The pharmaceutical composition according to embodiment 57-58 for use in medicine
60. The pharmaceutical composition according to embodiment 57-58 for use in the treatment of diabetes or obesity.
61. A method of treating diabetes in a patient in need thereof comprising administering to said patient a therapeutically effective amount of the product obtainable by the process of any one of embodiments 1-55, the product according to embodiment 56 or the pharmaceutical composition according to any one of embodiments 57-58.
62. A method of treating obesity in a patient in need thereof comprising administering to said patient a therapeutically effective amount of the product obtainable by the process of any one of embodiments 1-55, the product according to embodiment 56 or the pharmaceutical composition according to any one of embodiments 57-58.

EXAMPLES

General Methods
Laboratory Scale:

A feed solution of of semaglutide in an aqueous organic solvent was used for all laboratory scale experiments with concentrations given in each example.

Spray drying experiments were carried out on a Büchi B-290 laboratory scale spray dryer coupled with an inert loop B-295 for re-circulation of the drying gas. Nitrogen gas was used as atomising gas and as drying gas. A two fluid nozzle with 0.7 mm inside diameter and cap 1.5 mm in diameter was used for atomising.

Condenser temperature set point was at 5° C. for all experiments and solvent used for stabilisation corresponded to the aqueous organic solvent of the feed solution for each example.

The aspirator was switched on at 100%, followed by the nitrogen gas, at a level required for the given experiment conditions (22-39 mm Hg on the built-in rotameter, corresponding to 0.33-0.79 kg/h). When sufficiently low oxygen levels were reached (<6 vol %) inside the spray dryer, the heater was switched on at a set point of 90-100° C. to heat up the spray dryer (gas stabilisation). When the intended outlet temperature had been reached, the inlet temperature set point was increased (104-134° C.), followed by initiation of the feed solution flow and gradual increase to keep the target outlet temperature (solvent stabilisation). Once the target feed solution flow rate was reached (0.37 kg/h±0.06 kg/h), the actual target outlet temperature was acquired by fine tuning the inlet temperature (100-134° C., depending on the tested outlet temperature). Finally, all parameters were verified as required. Lower and upper limits for parameters used in the experiment, are shown in Table 1.

TABLE 1

Lower and upper limits of parameters varied in the laboratory scale experiments.

| Parameter | Lower limit | Upper limit |
| --- | --- | --- |
| Outlet temp ($T_{out}$) [° C.] | 68 | 88 |
| Atomising gas flow rate ($F_{atom}$) [kg/h] | 0.33 | 0.79 |
| Feed flow rate ($F_{feed}$) [kg/h] | 0.31 | 0.43 |
| Ratio ($F_{atom}/F_{feed}$) | 0.8 | 2.5 |
| Inlet temp ($T_{in}$) [° C.] | 104 | 134 |

Once a stable temperature profile was reached, the feeding tube of the spray dryer was transferred from the stabilisation solvent to the feed solution of semaglutide in the given aqueous organic solvent as described above to initiate the actual spray drying process. Product was collected by a high-performance cyclone connected to the drying chamber for 40-70 minutes. Yield was calculated as the collected material, taking into account the solvent/moisture levels obtained with a loss on drying method (LOD).

Production Scale:

A feed solution of 1-5% (w/w) of semaglutide in 42-60% (w/w) aqueous ethanol solvent was used for production scale experiments.

Spray drying experiments were carried out on a PSD4 manufacturing scale spray dryer using a two-fluid nozzle and nitrogen for atomisation. The two-fluid nozzle had 1.0 mm inside diameter and cap 6.5 mm in diameter. Nitrogen gas was also used as drying gas.

Solvent used for stabilisation matched the aqueous ethanol composition of the solution comprising semaglutide (42-60% (w/w)). Before batch initiation, the spray dryer was stabilized on the required set point values and the inlet temperature adjusted to obtain the desired outlet temperature. Lower and upper limits for parameters used in the production scale experiments, is shown in Table 2.

TABLE 2

Lower and upper limits of parameters varied in the production scale experiments.

| Parameter | Lower limit | Upper limit |
| --- | --- | --- |
| Outlet temp ($T_{out}$) [° C.] | 58 | 90 |
| Atomising gas flow rate ($F_{atom}$) [kg/h] | 38 | 65 |
| Feed flow rate ($F_{feed}$) [kg/h] | 35 | 56 |
| Ratio ($F_{atom}/F_{feed}$) | 0.7 | 1.8 |
| Inlet temp ($T_{in}$) [° C.] | 106 | 179 |
| Additional parameters | | |
| Condenser temp ($T_{cond}$) [° C.] | −5 | 5 |
| Drying gas flow ($F_{dry\ gas}$) [kg/h] | 1198 | 1748 |
| Semaglutide conc [w/w %] | 1 | 5 |
| Aq ethanol conc [w/w %] | 42 | 60 |

Once stable parameters were achieved, a switch was made from stabilisation solvent to the semaglutide feed solution to initiate the actual spray drying process. Product was collected for 1-71 hours using filter bag sleeves with filter bag blowback at pre-defined intervals. Yield was calculated as the collected material, taking into account the semaglutide content of the drug substance as acquired by RP-HPLC.

Example 1

Spray drying of a 2.1% (w/w) semaglutide solution in 53.5% (w/w) aqueous ethanol was conducted as described under General Methods—Laboratory scale. The results are presented in Table 3 and FIG. 1. The below data are based on a single experiment unless marked with * which is an average of 2 experiments. Purity of the collected material was analysed for selected experiments and no decomposition of product was observed.

TABLE 3

Data for laboratory scale experiments with semaglutide in aqueous ethanol.

| $T_{out}$ ° C. | $F_{atom}$ [kg/h] | $F_{feed}$ [kg/h] | Ratio $F_{atom}/F_{feed}$ | Ratio rounded | True yield % |
| --- | --- | --- | --- | --- | --- |
| 68 | 0.38 | 0.39 | 0.98 | 1.0 | 86.5 |
| | 0.38 | 0.37 | 1.03 | 1.0 | 87.3 |
| | 0.52 | 0.37 | 1.42 | 1.4 | 90.3 |
| | 0.67 | 0.37 | 1.84 | 1.8 | 86.0 |
| | 0.67 | 0.35 | 1.95 | 2.0 | 87.8 |
| | 0.79 | 0.31 | 2.51 | 2.5 | 85.2 |
| 73 | 0.33 | 0.39 | 0.84 | 0.8 | 78.8 |
| | 0.38 | 0.39 | 0.98 | 1.0 | 89.6 |
| | 0.38 | 0.38 | 1.02 | 1.9 | 86.0 |
| | 0.47 | 0.40 | 1.19 | 1.2 | 93.9 |
| | 0.52 | 0.40 | 1.29 | 1.3 | 95.0 |
| | 0.52 | 0.40 | 1.29 | 1.3 | 93.5 |
| | 0.52 | 0.40 | 1.31 | 1.3 | 94.0 |
| | 0.61 | 0.41 | 1.48 | 1.5 | 92.8 |
| | 0.67 | 0.40 | 1.68 | 1.7 | 91.6 |
| 76 | 0.61 | 0.40 | 1.52 | 1.5 | 95.3 |
| 78 | 0.47 | 0.41 | 1.14 | 1.1 | 94.2 |
| | 0.58 | 0.36 | 1.60 | 1.6 | 94.9 |
| | 0.67 | 0.41 | 1.66 | 1.7 | 88.7 |

TABLE 3-continued

Data for laboratory scale experiments with semaglutide in aqueous ethanol.

| $T_{out}$ °C. | $F_{atom}$ [kg/h] | $F_{feed}$ [kg/h] | Ratio $F_{atom}/F_{feed}$ | Ratio rounded | True yield % |
|---|---|---|---|---|---|
| 83 | 0.38 | 0.39 | 0.99 | 1.0 | 88.8 |
|  | 0.52 | 0.40 | 1.31 | 1.3 | 95.5 |
|  | 0.52 | 0.40 | 1.32 | 1.3 | 93.3 |
|  | 0.52 | 0.35 | 1.48 | 1.5 | 93.8 |
|  | 0.67 | 0.38 | 1.76 | 1.8 | 86.3 |
|  | 0.67 | 0.35 | 1.91 | 1.9 | 89.9 |
|  | 0.79 | 0.40 | 1.99 | 2.0 | 87.6 |
| 88 | 0.79 | 0.35 | 2.23 | 2.2 | 86.4 |

The results presented in Table 3 and FIG. 1 shows that when the ratio of atomising gas flow rate (kg/h)/feed flow rate (kg/h) is between approx. 1.1-1.7 a higher yield is obtained compared to experiments performed outside the specified ratio.

Example 2

Spray drying of semaglutide was conducted as described under General Methods—Production scale varying the parameters as shown in Table 2. The results are presented in Table 4 and FIG. 2. The below data are based on single experiments. Purity of the collected material was analysed for selected experiments and no decomposition of product was observed.

TABLE 4

Data for production scale experiments with semaglutide in aqueous ethanol.

| $T_{out}$ [° C.] | $F_{dry\,gas}$ [kg/h] | $T_{in}$ [° C.] | $T_{cond}$ [° C.] | EtOH [w/w %] | Sema Conc. [w/w %] | $F_{atom}$ [kg/h] | $F_{feed}$ [kg/h] | Ratio ($F_{atom}/F_{feed}$) | Ratio round | True yield % |
|---|---|---|---|---|---|---|---|---|---|---|
| 58 | 1343 | 137 | 0 | 42 | 4.9 | 38 | 56 | 0.68 | 0.7 | 51.6 |
|  | 1347 | 137 | 0 | 48 | 2.3 | 38 | 56 | 0.68 | 0.7 | 51.6 |
|  | 1345 | 128 | 0 | 58 | 2.4 | 38 | 56 | 0.68 | 0.7 | 57.5 |
|  | 1345 | 138 | 0 | 42 | 2.4 | 38 | 56 | 0.68 | 0.7 | 47.1 |
|  | 1347 | 133 | 0 | 46 | 5.1 | 38 | 56 | 0.69 | 0.7 | 53.0 |
|  | 1351 | 109 | 0 | 52 | 2.1 | 60 | 36 | 1.67 | 1.7 | 97.4 |
|  | 1350 | 110 | 0 | 50 | 1.0 | 60 | 36 | 1.67 | 1.7 | 86.1 |
|  | 1349 | 106 | 0 | 60 | 1.0 | 60 | 36 | 1.67 | 1.7 | 78.2 |
|  | 1349 | 109 | 0 | 48 | 2.3 | 60 | 36 | 1.68 | 1.7 | 81.8 |
|  | 1347 | 108 | 0 | 46 | 5.1 | 60 | 35 | 1.70 | 1.7 | 78.7 |
|  | 1350 | 111 | 0 | 52 | 2.1 | 64 | 36 | 1.77 | 1.8 | 49.4 |
| 59 | 1350 | 140 | 0 | 52 | 2.1 | 38 | 56 | 0.68 | 0.7 | 74.9 |
| 67 | 1348 | 134 | 0 | 48 | 2.3 | 45 | 46 | 0.98 | 1.0 | 72.9 |
| 68 | 1348 | 129 | 0 | 58 | 2.4 | 45 | 46 | 0.98 | 1.0 | 77.1 |
|  | 1350 | 135 | 0 | 48 | 2.3 | 45 | 46 | 0.98 | 1.0 | 76.6 |
|  | 1198 | 142 | 0 | 48 | 2.3 | 45 | 46 | 0.98 | 1.0 | 66.3 |
|  | 1349 | 136 | −5 | 48 | 2.3 | 45 | 46 | 0.98 | 1.0 | 72.3 |
|  | 1348 | 135 | 5 | 48 | 2.3 | 45 | 46 | 0.98 | 1.0 | 70.7 |
|  | 1350 | 135 | 0 | 48 | 2.3 | 45 | 46 | 0.98 | 1.0 | 85.9 |
|  | 1349 | 136 | 0 | 48 | 2.3 | 45 | 46 | 0.98 | 1.0 | 72.9 |
|  | 1354 | 133 | 0 | 53 | 2.1 | 45 | 46 | 0.98 | 1.0 | 80.8 |
|  | 1353 | 133 | 0 | 53 | 2.1 | 46 | 46 | 0.99 | 1.0 | 78.4 |
|  | 1749 | 119 | 0 | 48 | 2.3 | 45 | 46 | 0.98 | 1.0 | 64.6 |
|  | 1348 | 137 | 0 | 42 | 2.4 | 45 | 46 | 0.98 | 1.0 | 75.6 |
|  | 1349 | 135 | 0 | 50 | 1.0 | 45 | 46 | 0.98 | 1.0 | 86.7 |
|  | 1350 | 134 | 0 | 52 | 2.1 | 45 | 46 | 0.98 | 1.0 | 82.0 |
|  | 1347 | 130 | 0 | 60 | 1.0 | 45 | 46 | 0.98 | 1.0 | 69.9 |
|  | 1350 | 131 | 0 | 53 | 2.3 | 45 | 46 | 0.98 | 1.0 | 76.1 |
|  | 1347 | 135 | 0 | 42 | 4.9 | 45 | 46 | 0.98 | 1.0 | 74.1 |
|  | 1346 | 134 | 0 | 46 | 5.1 | 45 | 46 | 0.99 | 1.0 | 66.4 |
| 73 | 1351 | 140 | 0 | 50 | 2.0 | 57 | 46 | 1.24 | 1.2 | 94.8 |
|  | 1355 | 137 | 0 | 53 | 2.0 | 57 | 46 | 1.25 | 1.2 | 90.7 |
|  | 1350 | 139 | 0 | 53 | 2.1 | 57 | 46 | 1.24 | 1.2 | 91.8 |
| 78 | 1348 | 161 | 0 | 48 | 2.3 | 38 | 56 | 0.68 | 0.7 | 63.8 |
|  | 1351 | 133 | 0 | 52 | 2.1 | 38 | 36 | 1.06 | 1.1 | 90.3 |
|  | 1349 | 134 | 0 | 48 | 2.3 | 38 | 36 | 1.06 | 1.1 | 83.9 |
|  | 1351 | 161 | 0 | 52 | 2.1 | 60 | 56 | 1.07 | 1.1 | 97.1 |
|  | 1347 | 162 | 0 | 48 | 2.3 | 60 | 56 | 1.07 | 1.1 | 80.8 |
| 79 | 1349 | 163 | 0 | 52 | 2.1 | 38 | 56 | 0.68 | 0.7 | 72.4 |
|  | 1350 | 136 | 0 | 46 | 5.1 | 38 | 36 | 1.06 | 1.1 | 76.4 |
|  | 1346 | 161 | 0 | 46 | 5.1 | 60 | 56 | 1.08 | 1.1 | 76.6 |
| 89 | 1350 | 178 | 0 | 52 | 2.1 | 38 | 56 | 0.68 | 0.7 | 74.6 |
| 90 | 1350 | 149 | 0 | 52 | 2.1 | 38 | 36 | 1.06 | 1.1 | 104.1 |

Figure 2:
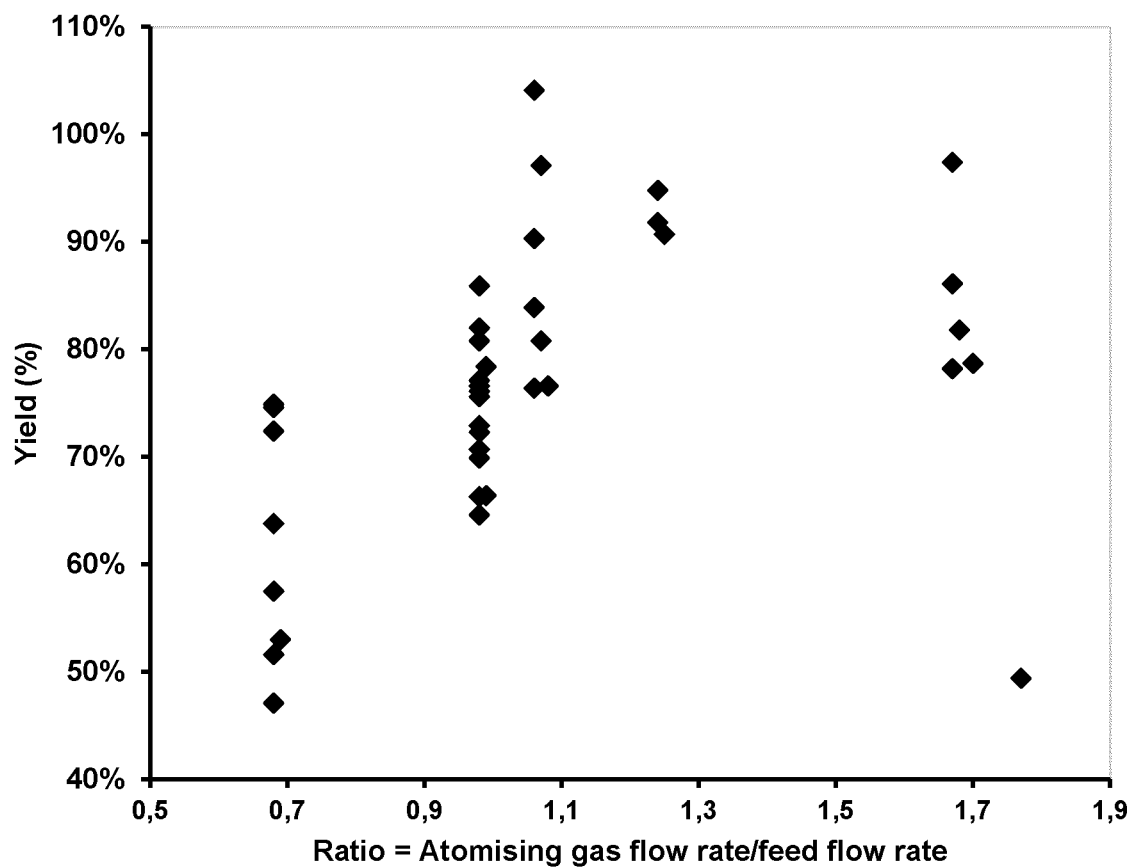
FIG. 2 is a plot of the data from production scale experiments of semaglutide in aqueous ethanol (Example 2, Table 4). It is seen that when the ratio of atomising gas flow rate/feed flow rate is between 1.0-1.7, then a higher yield is obtained compared to experiments performed outside the specified ratio.

The results presented in Table 4 and FIG. 2 shows that when the ratio of atomising gas flow rate/feed flow rate is between 1.0-1.7 a higher yield is obtained compared to experiments performed outside the specified ratio.

A standard least square data analysis using SAS JMP® software (version 12.2) of the data in Table 4 shows that the ratio of atomising gas flow (kg/h) to feed flow rate (kg/h) has a significant influence on yield within the interval of 1.0-1.7.

Example 3

Spray drying of a 2.1% (w/w) semaglutide solution in 53.5% (w/w) aqueous acetonitrile was conducted as described under General Methods—Laboratory scale. The results are presented in Table 5 and FIG. 3. The below data are based on a single experiment. Purity of the collected material was analysed for selected experiments and no decomposition of product was observed.

TABLE 5

Data for laboratory scale experiments with semaglutide in aqueous acetonitrile.

| $T_{out}$ °C. | $F_{atom}$ [kg/h] | $F_{feed}$ [kg/h] | Ratio $F_{atom}/F_{feed}$ | True yield % |
|---|---|---|---|---|
| 68 | 0.522 | 0.417 | 1.3 | 92.0 |
| 73 | 0.330 | 0.394 | 0.8 | 78.5 |
| 78 | 0.674 | 0.433 | 1.6 | 89.8 |
|  | 0.578 | 0.430 | 1.3 | 92.4 |
| 83 | 0.385 | 0.354 | 1.1 | 89.1 |
|  | 0.674 | 0.417 | 1.6 | 88.2 |

Figure 3:
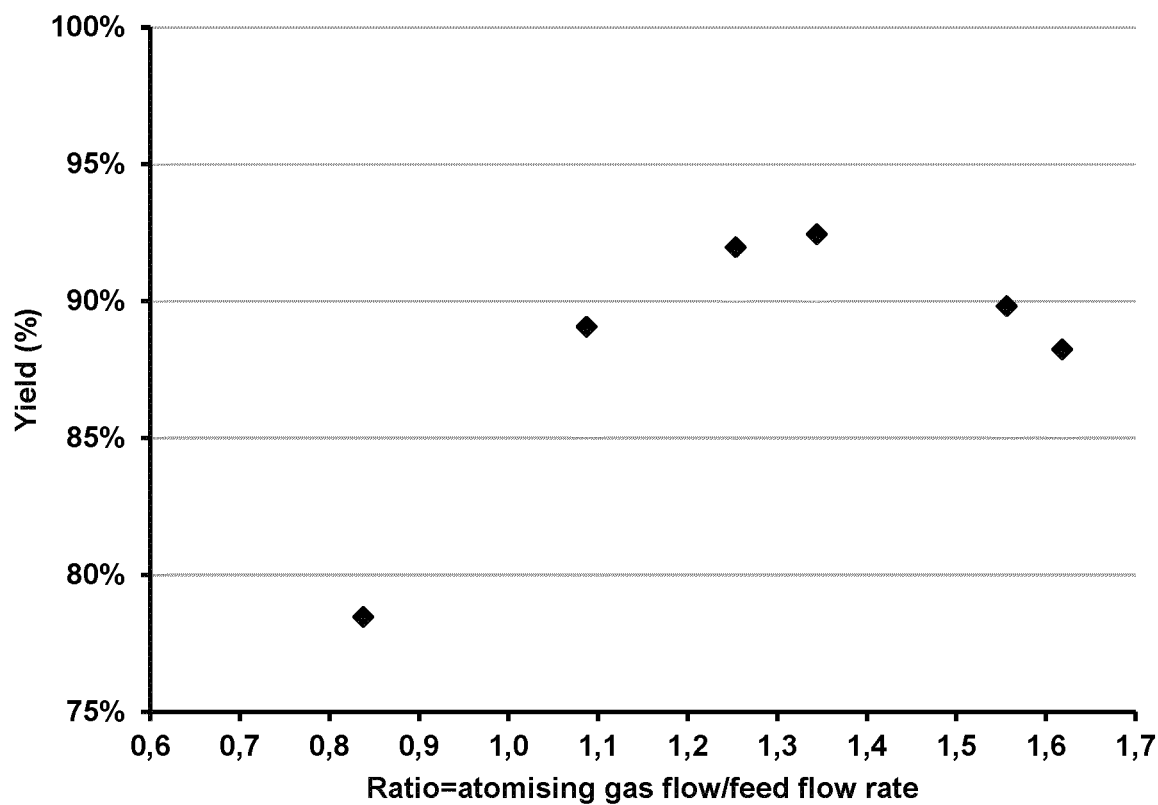
FIG. 3 is a plot of the data from laboratory scale experiments of semaglutide in aqueous acetonitrile (Example 3, Table 5). It is seen that when the ratio of atomising gas flow rate (kg/h)/feed flow rate (kg/h) is between 1.0-1.7, then a higher yield is obtained compared to experiments performed outside the specified ratio.

The results presented in Table 5 and FIG. 3 shows that when the ratio of atomising gas flow rate (kg/h)/feed flow rate (kg/h) is within the interval of 1.0-1.7 a higher yield is obtained compared to the experiment performed outside the specified ratio.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A process for spray drying a feed solution comprising semaglutide, the process comprising:
    introducing the feed solution into a spray dryer at a feed flow rate and
    introducing an atomising gas into the spray dryer at an atomising gas flow rate,
    wherein the feed solution comprises semaglutide in a solvent, and
    wherein the ratio of the atomising gas flow rate (kg/h) to the feed flow rate (kg/h) is in the range of 1.0-1.7.

2. The process according to claim 1, wherein the ratio of the atomising gas flow rate (kg/h) to the feed flow rate (kg/h) is in the range of 1.1-1.7.

3. The process according to claim 1, wherein the feed flow rate is 20-60 kg/h.

4. The process according to claim 1, wherein the feed flow rate is 41-51 kg/h.

5. The process according to claim 1, wherein the atomising gas flow rate is 20-80 kg/h.

6. The process according to claim 1, wherein the atomising gas flow rate is 52-62 kg/h.

7. The process according to claim 1, wherein the feed solution comprises 0.5-10% (w/w) semaglutide in 40-70% (w/w) aqueous organic solvent.

8. The process according to claim 7, wherein the aqueous organic solvent is selected from the list consisting of aqueous ethanol and aqueous acetonitrile.

9. The process according to claim 7, wherein the feed solution comprises 1-5% (w/w) semaglutide.

10. The process according to claim 7, wherein the feed solution comprises 1-3% (w/w) semaglutide.

11. The process according to claim 7, wherein the feed solution comprises 45-60% (w/w) aqueous organic solvent.

12. The process according to claim 7, wherein the feed solution comprises 48-55% (w/w) aqueous organic solvent.

13. The process according to claim 7, wherein the feed solution comprises 2.0-2.5% (w/w) semaglutide in 48-53% (w/w) aqueous ethanol.

14. The process according to claim 7, wherein the feed solution comprises 2.0-2.5% (w/w) semaglutide in 50-55% (w/w) aqueous acetonitrile.

15. The process according to claim 1, wherein the spray dryer further comprises an outlet, wherein the temperature of outlet is 50-100° C.

16. The process according to claim 15, wherein the temperature of the outlet is 60-90° C.

17. The process according to claim 1, wherein the spray dryer further comprises an inlet, wherein the temperature of the inlet is 85-200° C.

18. The process according to claim 1, further comprising introducing a drying gas, wherein the drying gas flow rate is 1000-1800 kg/h.

19. The process according to claim 1, wherein the spray dryer further comprises a nozzle, and wherein the nozzle comprises at least two-fluid entry channels.

20. The process according to claim 19, wherein the nozzle is a two-fluid nozzle.

21. The process according to claim 1, wherein the spray dryer further comprises an outlet,
    wherein the feed solution consists essentially of 2.0-2.2% (w/w) semaglutide in 50-55% (w/w) aqueous ethanol,
    wherein the feed solution is introduced into the spray dryer at a feed flow rate of 40-50 kg/h,
    wherein the atomising gas is introduced into the spray dryer at an atomising gas flow rate of 55-60 kg/h,
    wherein a drying gas is introduced into the spray dryer at a drying gas flow rate of 1345-1355 kg/h,
    wherein the temperature of the outlet 70-75° C.,
    and wherein the drying gas and the atomising gas are both nitrogen.

22. The process according to claim 1, wherein the ratio of the atomising gas flow rate (kg/h) to the feed flow rate (kg/h) is in the range of 1.2-1.7.

23. The process according to claim 1, wherein the spray dryer further comprises an outlet,
    wherein the feed solution comprises 2.0-2.2% (w/w) semaglutide in 50-55% (w/w) aqueous ethanol,
    wherein the feed solution is introduced into the spray dryer at a feed flow rate of 40-50 kg/h,
    wherein the atomising gas is introduced into the spray dyer at an atomising gas flow rate of 55-60 kg/h,
    wherein a drying gas is introduced into the spray dryer at a drying gas flow rate of 1345-1355 kg/h,
    wherein the temperature of the outlet is 70-75° C.

24. The process according to claim 23, wherein the spray dryer further comprises an inlet, and
    wherein the temperature of the inlet is 120-160° C.

25. The process according to claim 23, wherein the drying gas and the atomising gas are both nitrogen.

26. The process according to claim 1, wherein the spray dryer further comprises an inlet and an outlet,
- wherein the feed solution comprises 1-5% (w/w) semaglutide in 42-60% (w/w) aqueous ethanol,
- wherein the feed solution is introduced into the spray dryer at a feed flow rate of 35-56 kg/h,
- wherein the atomising gas is introduced into the spray dyer at an atomising gas flow rate of 38-65 kg/h,
- wherein a drying gas is introduced into the spray dryer at a drying gas flow rate of 1198-1748 kg/h,
- wherein the temperature of the outlet is 58-90° C., and
- wherein the temperature of the inlet is 106-179° C.

* * * * *